United States Patent
Chen et al.

(10) Patent No.: US 12,077,511 B2
(45) Date of Patent: Sep. 3, 2024

(54) ORGANIC AMINE SALT OF KEY INTERMEDIATE OF ELAGOLIX SODIUM AND PREPARATION METHOD THEREOF

(71) Applicant: NANJING CHEMPION BIOTECHNOLOGY CO., LTD., Nanjing (CN)

(72) Inventors: Jian Chen, Nanjing (CN); Xianqiang Zhang, Nanjing (CN); Yaoqiang Li, Nanjing (CN)

(73) Assignee: Nanjing Chempion Biotechnology Co., Ltd., Nanjing (CN)

( * ) Notice: Subject to any disclaimer, the term of this patent is extended or adjusted under 35 U.S.C. 154(b) by 662 days.

(21) Appl. No.: 17/426,522

(22) PCT Filed: Nov. 24, 2020

(86) PCT No.: PCT/CN2020/131054
§ 371 (c)(1),
(2) Date: Jul. 28, 2021

(87) PCT Pub. No.: WO2022/032927
PCT Pub. Date: Feb. 17, 2022

(65) Prior Publication Data
US 2022/0242830 A1 Aug. 4, 2022

(30) Foreign Application Priority Data
Aug. 12, 2020 (CN) .......................... 202010828575.8

(51) Int. Cl.
*C07D 239/54* (2006.01)
(52) U.S. Cl.
CPC .................. *C07D 239/54* (2013.01)
(58) Field of Classification Search
CPC ................................................ C07D 239/54
USPC ........................................................ 544/311
See application file for complete search history.

(56) References Cited

FOREIGN PATENT DOCUMENTS

| CN | 109651171 A | 4/2019 |
| WO | 2020/023459 A1 | 1/2020 |

OTHER PUBLICATIONS

China National Intellectual Property Administration, International Search Report issued in corresponding Application No. PCT/CN2020/131054 dated May 19, 2021. (Translation not available.).

*Primary Examiner* — Taofiq A Solola
(74) *Attorney, Agent, or Firm* — Patrick M. Torre; Stites & Harbison, PLLC

(57) ABSTRACT

The present disclosure discloses a compound 1,1,3,3-tetramethylguanidine (R)-(tert-butoxycarbonyl)(2-(5-(2-fluoro-3-methoxyphenyl)-3-(2-fluoro-6-(trifluoromethyl)benzyl)-4-methyl-2,6-dicarbonyl-3,6-dihydropyrimidine-1(2H)-yl)-1-phenylethyl) sulfamate (of structural formula I) and a preparation method thereof.

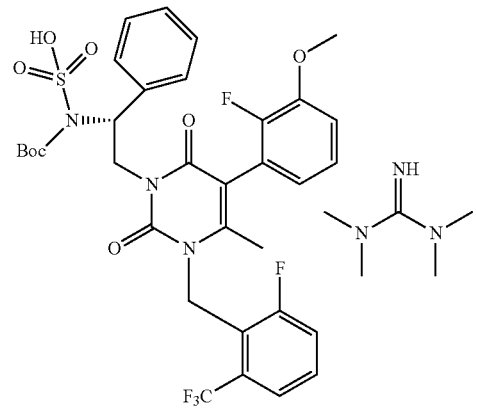

6 Claims, No Drawings

ORGANIC AMINE SALT OF KEY INTERMEDIATE OF ELAGOLIX SODIUM AND PREPARATION METHOD THEREOF

CROSS REFERENCE TO RELATED APPLICATIONS

The present application claims priority to international patent application no. PCT/CN2020/131054 filed on Nov. 24, 2020, which in turn claims priority to Chinese Patent Application No. 202010828575.8 filed to the China National Intellectual Property Administration on Aug. 12, 2020 and entitled "organic amine salt of key intermediate of Elagolix sodium and preparation method thereof," the disclosures of each of which are incorporated herein by reference in their entirety.

TECHNICAL FIELD

The present disclosure relates to 1,1,3,3-tetramethylguanidine(R)-(tert-butoxycarbonyl)(2-(5-(2-fluoro-3-methoxyphenyl)-3-(2-fluoro-6-(trifluoromethyl)benzyl)-4-methyl-2,6-dicarbonyl-3,6-dihydropyrimidine-1(2H)-yl)-1-phenylethyl) sulfamate as an intermediate for preparation of a drug, and a preparation method thereof.

BACKGROUND ART

Elagolix sodium (of structural formula V) is an orally-administrated non-peptide micromolecule gonadotrophin-releasing hormone (GnRH) receptor antagonist, which inhibits endogenous GnRH signaling by competitively binding with a GnRH receptor in a pituitary gland. Administration of Elagolix sodium will cause dose-dependent inhibition of a luteinizing hormone and a follicle-stimulating hormone, and reduce the plasma concentrations of ovarian sex hormone, estradiol and progesterone. In July, 2018, the drug was approved by FDA to treat women with moderate to severe endometriosis pain. It is worth mentioning that Elagolix sodium is the first oral therapy approved by FDA for this indication in ten years.

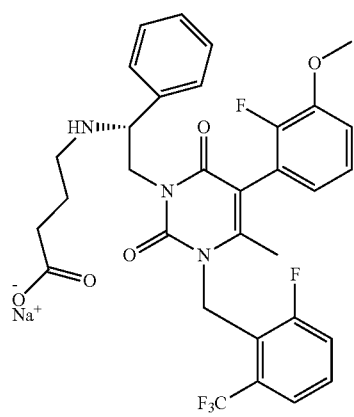

V

Currently, a main route for synthesis of Elagolix sodium is the compound synthetic route reported in patent CN100424078C, as shown below:

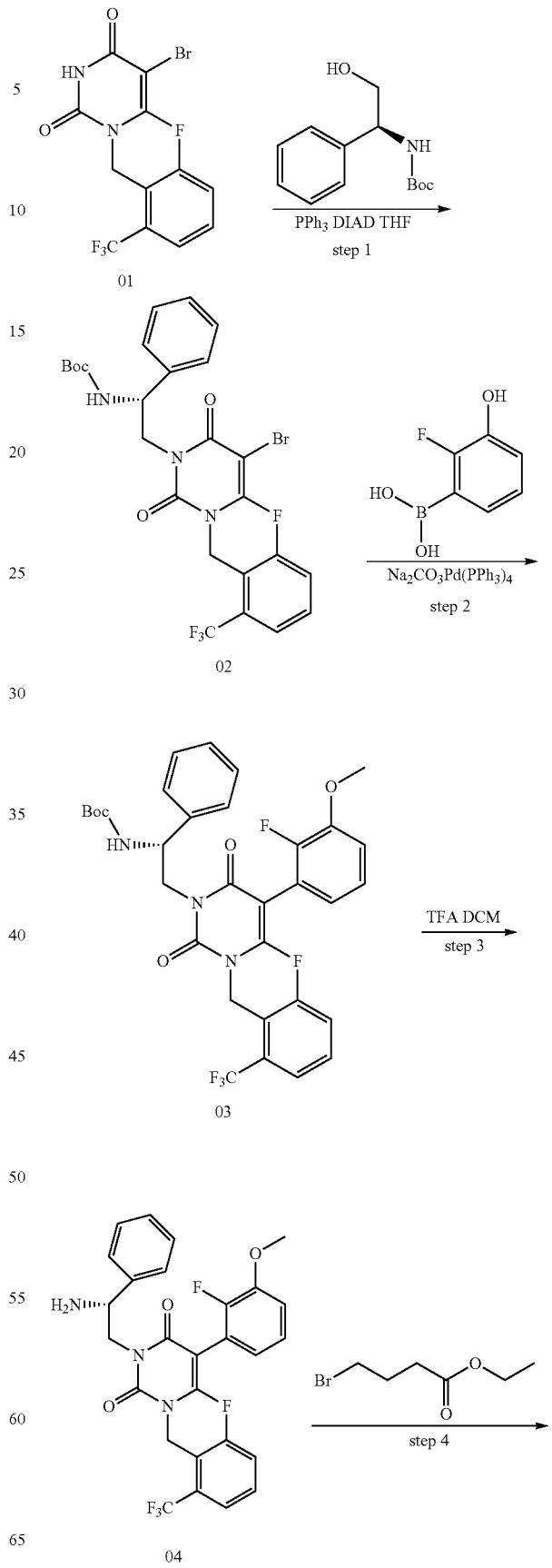

-continued
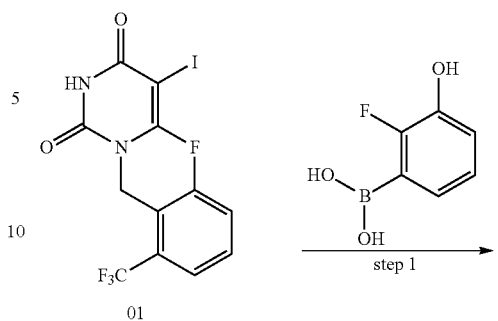
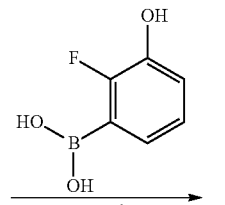
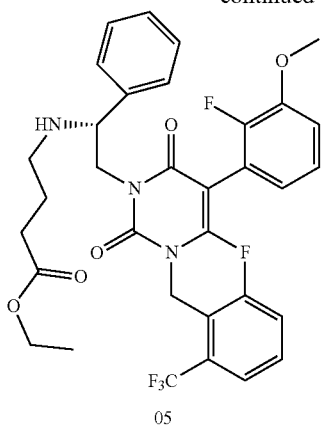
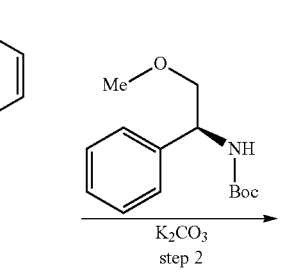
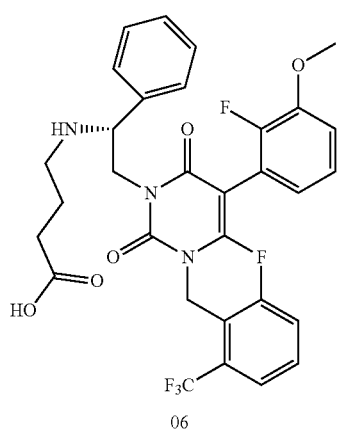
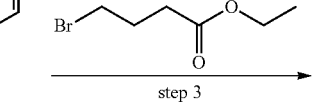
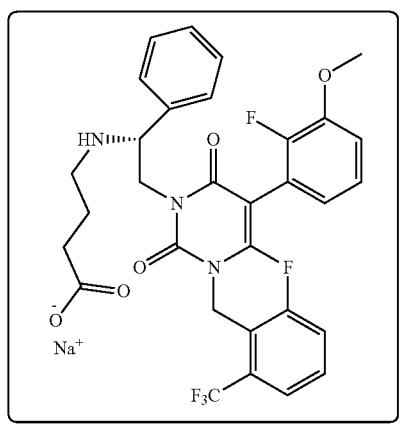
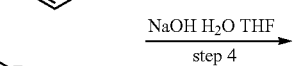
In the reported compound synthetic route, intermediates obtained in multiple steps are oily, and cannot be recrystallized and refined, resulting in difficulty in purification. Further, the producer of reference listed drugs, AbbVie, has developed a patent process route of this compound (patent WO2009062087) as shown below:

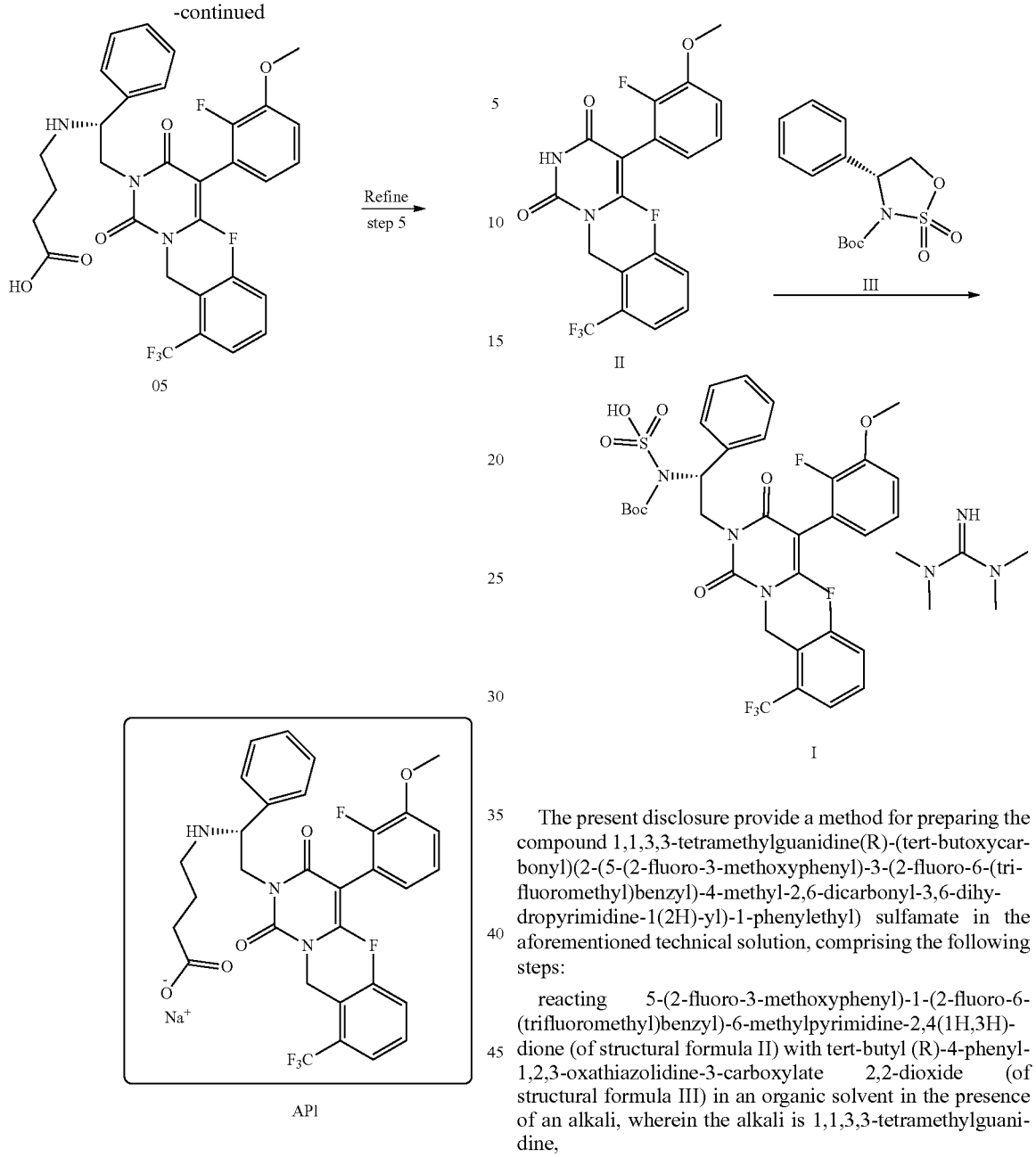

API

On the basis of the compound patent, this route has improved process on multiple steps, but is still difficult to solve the problem of intermediate purification. After multiple steps, a solution of crude products is directly obtained, and is then subjected to a subsequent reaction, which brings about certain challenges to the quality control and process stability of an active pharmaceutical ingredient (API).

SUMMARY

The present disclosure provides a compound 1,1,3,3-tetramethylguanidine(R)-(tert-butoxycarbonyl)(2-(5-(2-fluoro-3-methoxyphenyl)-3-(2-fluoro-6-(trifluoromethyl)benzyl)-4-methyl-2,6-dicarbonyl-3,6-dihydropyrimidine-1(2H)-yl)-1-phenylethyl) sulfamate with a structure of formula I.

The present disclosure provide a method for preparing the compound 1,1,3,3-tetramethylguanidine(R)-(tert-butoxycarbonyl)(2-(5-(2-fluoro-3-methoxyphenyl)-3-(2-fluoro-6-(trifluoromethyl)benzyl)-4-methyl-2,6-dicarbonyl-3,6-dihydropyrimidine-1(2H)-yl)-1-phenylethyl) sulfamate in the aforementioned technical solution, comprising the following steps:

reacting 5-(2-fluoro-3-methoxyphenyl)-1-(2-fluoro-6-(trifluoromethyl)benzyl)-6-methylpyrimidine-2,4(1H,3H)-dione (of structural formula II) with tert-butyl (R)-4-phenyl-1,2,3-oxathiazolidine-3-carboxylate 2,2-dioxide (of structural formula III) in an organic solvent in the presence of an alkali, wherein the alkali is 1,1,3,3-tetramethylguanidine,

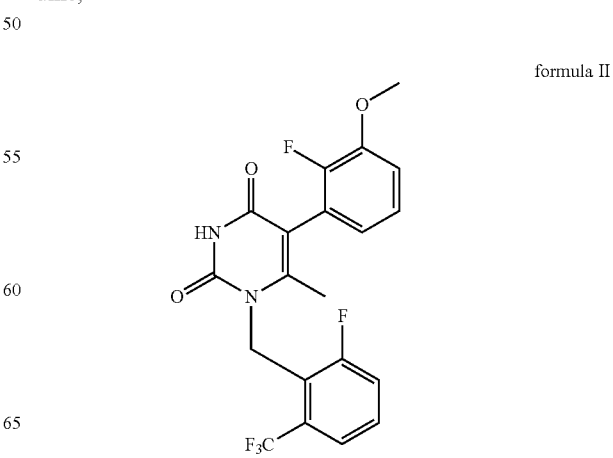

formula II

-continued

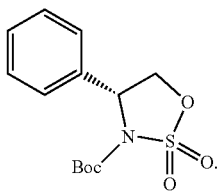

formula III

In some embodiments, the organic solvent is selected from the group consisting of acetonitrile, tetrahydrofuran, N,N-dimethylformamide, and dimethyl sulfoxide.

In some embodiments, the reacting is carried out at a temperature of 60° C. for 16 hours.

In some embodiments, the method further comprises: after the reaction, concentrating the resulting reaction solution to dryness, adding 2-methyltetrahydrofuran, and conducting a recrystallization, to obtain 1,1,3,3-tetramethylguanidine(R)-(tert-butoxycarbonyl)(2-(5-(2-fluoro-3-methoxyphenyl)-3-(2-fluoro-6-(trifluoromethyl)benzyl)-4-methyl-2,6-dicarbonyl-3,6-dihydropyrimidine-1(2H)-yl)-1-phenylethyl) sulfamate.

In view of the problem of difficulty in purification caused by the oily intermediates obtained in multiple steps of the current method for preparing Elagolix sodium, the inventor of the present disclosure has studied the process route and unexpectedly found that the intermediate 1,1,3,3-tetramethylguanidine(R)-(tert-butoxycarbonyl)(2-(5-(2-fluoro-3-methoxyphenyl)-3-(2-fluoro-6-(trifluoromethyl)benzyl)-4-methyl-2,6-dicarbonyl-3,6-dihydropyrimidine-1(2H)-yl)-1-phenylethyl) sulfamate (of structural formula I) is a solid with a good crystallization performance, and the preparation method thereof is simple, and has a good conversion rate, and good atom economy. Since the compound 1,1,3,3-tetramethylguanidine(R)-(tert-butoxycarbonyl)(2-(5-(2-fluoro-3-methoxyphenyl)-3-(2-fluoro-6-(trifluoromethyl)benzyl)-4-methyl-2,6-dicarbonyl-3,6-dihydropyrimidine-1(2H)-yl)-1-phenylethyl) sulfamate (of structural formula I) has a good crystallization performance, it is possible to obtain an intermediate with high purity by recrystallization, which could provide a good foundation for subsequent reaction and transformation, and further obtain Elagolix sodium (API) with a better quality and higher controllability.

DETAILED DESCRIPTION OF THE EMBODIMENTS

The following examples and preparation examples are described to illustrate the present disclosure, but the present disclosure is not limited thereto.

The raw materials and devices used in the examples of the present disclosure are all known products, which were obtained by purchasing commercially available products.

Example 1

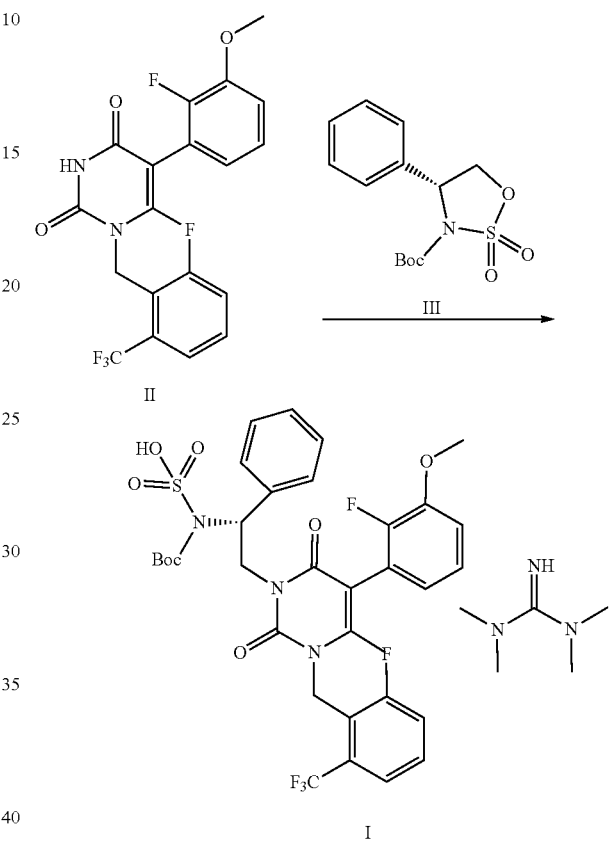

5-(2-fluoro-3-methoxyphenyl)-1-(2-fluoro-6-(trifluoromethyl)benzyl)-6-methyl pyrimidine-2,4(1H,3H)-dione (of structural formula II, 70.06 g, 1.0 equivalent), tert-butyl(R)-4-phenyl-1,2,3-oxathiazolidine-3-carboxylate 2,2-dioxide (of structural formula III, 54.06 g, 1.1 equivalents) and acetonitrile (350 mL) were added sequentially into a 2 L three-necked reaction flask, and were stirred at ambient temperature, and then 1,1,3,3-tetramethylguanidine (28.36 g, 1.5 equivalents) was added, and the resulting reaction system was heated to 60° C. for 16 hours. After TLC showed that the raw materials were completely converted, the reaction solution was concentrated to dryness, and 2-methyltetrahydrofuran (200 mL) was then added thereto, and the resulting mixture was subjected to a recrystallization, to obtain a product 1,1,3,3-tetramethylguanidine(R)-(tert-butoxycarbonyl)(2-(5-(2-fluoro-3-methoxyphenyl)-3-(2-fluoro-6-(trifluoromethyl)benzyl)-4-methyl-2,6-dicarbonyl-3,6-dihydropyrimidine-1(2H)-yl)-1-phenylethyl) sulfamate (of structural formula I, 122.8 g, yield of 89%, off-white solid).

1H-NMR (300 MHz, $d_6$-DMSO) δ 7.77-7.14 (m, 11H), 7.00-6.93 (d, 1H), 5.76 (s, 1H), 5.51-5.39 (m, 1H), 5.27-5.14 (m, 1H), 5.08-4.87 (m, 1H), 4.39-4.24 (m, 1H), 3.85 (s, 3H), 2.88 (s, 12H), 2.06 (s, 3H), 1.10 (s, 9H).

LCMS (ESI) m/z, 645.6 (M+1)$^+$.

Example 2

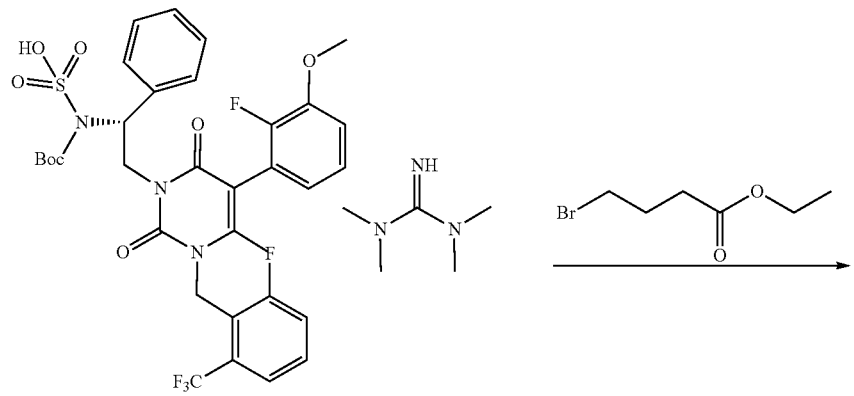

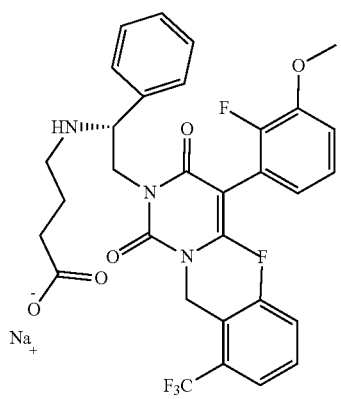

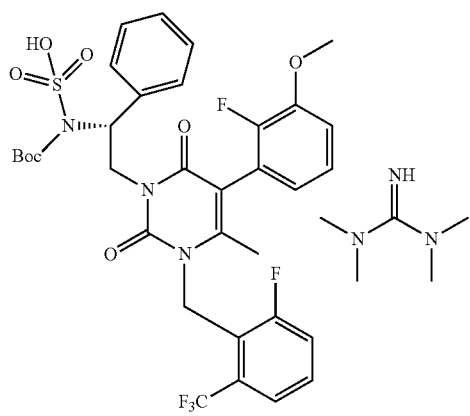

1,1,3,3-tetramethylguanidine(R)-(tert-butoxycarbonyl) (2-(5-(2-fluoro-3-methoxyphenyl)-3-(2-fluoro-6-(trifluoromethyl)benzyl)-4-methyl-2,6-dicarbonyl-3,6-dihydropyrimidine-1(2H)-yl)-1-phenylethyl)sulfamate (of structural formula I, 70 g), ethanol (385 mL), water (300 mL) and concentrated hydrochloric acid (97 mL) were added sequentially into a 2 L reaction flask and stirred at 50° C. for 4 hours, and the resulting reactant was adjusted to a pH value of 7-8 with sodium carbonate, and extracted and concentrated with isopropyl acetate to obtain an oily matter. The oily matter was mixed with ethyl bromobutyrate (16 g) and potassium carbonate (20 g) and DMF (300 mL). Then the resulting mixture was heated to 70° C. for 48 hours. The reactant was cooled to ambient temperature, added with NaOH (1N, 300 mL) and stirred at ambient temperature for 3 hours, and then extracted with isopropyl acetate, and the resulting aqueous phase was extracted with methyl isobutyl ketone. The methyl isobutyl ketone phase was collected and concentrated to obtain the product Elagolix sodium (44.6 g, off-white solid, yield of 82.0%).

The above description is only preferred embodiments of the present disclosure. It should be pointed out that, for those of ordinary skill in the art, several improvements and modifications could be made without departing from the principle of the present disclosure. These improvements and modifications should also be considered as falling into the protection scope of the present disclosure.

What is claimed is:

1. A compound 1,1,3,3-tetramethylguanidine(R)-(tert-butoxycarbonyl) (2-(5-(2-fluoro-3-methoxyphenyl)-3-(2-fluoro-6-(trifluoromethyl)benzyl)-4-methyl-2,6-dicarbonyl-3,6-dihydropyrimidine-1(2H)-yl)-1-phenylethyl) sulfamate with a structure of formula I:

formula I

2. A method for preparing the compound 1,1,3,3-tetramethylguanidine(R)-(tert-butoxycarbonyl)(2-(5-(2-fluoro-3-methoxyphenyl)-3-(2-fluoro-6-(trifluoromethyl)benzyl)-4- methyl-2,6-dicarbonyl-3,6-dihydropyrimidine-1(2H)-yl)-1-phenylethyl) sulfamate of claim 1, comprising the following steps:

reacting 5-(2-fluoro-3-methoxyphenyl)-1-(2-fluoro-6-(trifluoromethyl)benzyl)-6-methylpyrimidine-2,4(1H,3H)-dione of formula II with tert-butyl (R)-4-phenyl-1,2,3-oxathiazolidine-3-carboxylate 2,2-dioxide of formula III in an organic solvent in the presence of an alkali, wherein the alkali is 1,1,3,3-tetramethylguanidine,

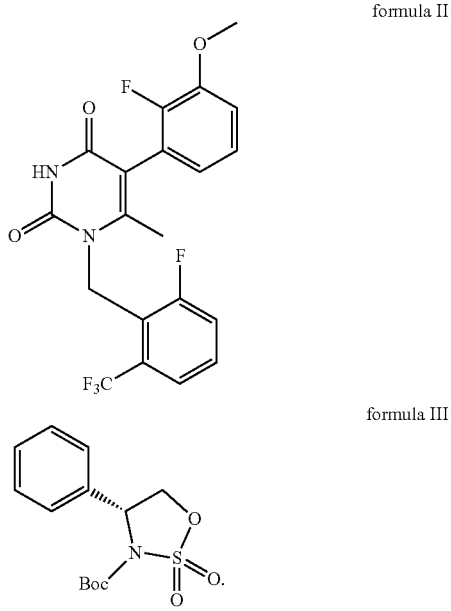

formula II formula III

3. The method of claim 2, wherein the organic solvent is selected from the group consisting of acetonitrile, tetrahydrofuran, N,N-dimethylformamide, and dimethyl sulfoxide.

4. The method of claim 2, wherein the reacting is carried out at a temperature of 60° C. for 16 hours.

5. The method of claim 2, wherein the method further comprises: after the reaction, concentrating the resulting reaction solution to dryness, adding 2-methyltetrahydrofuran, and conducting a recrystallization, to obtain 1,1,3,3-tetramethylguanidine(R)-(tert-butoxycarbonyl)(2-(5-(2-fluoro-3-methoxyphenyl)-3-(2-fluoro-6-(trifluoromethyl)benzyl)-4-methyl-2,6-dicarbonyl-3,6-dihydropyrimidine-1(2H)-yl)-1-phenylethyl) sulfamate.

6. A method for preparing Elagolix sodium, comprising the following steps:

sequentially mixing 70 g of 1,1,3,3-tetramethylguanidine (R)-(tert-butoxycarbonyl)(2-(5-(2-fluoro-3-methoxyphenyl)-3-(2-fluoro-6-(trifluoromethyl)benzyl)-4-methyl-2,6-dicarbonyl-3,6-dihydropyrimidine-1(2H)-yl)-1-phenylethyl) sulfamate of claim 1 with 385 mL of ethanol, 300 mL of water and 97 mL of concentrated hydrochloric acid, to obtain a mixture;

stirring the mixture at 50° C. for 4 hours, adjusting the mixture to a pH value of 7-8 with sodium carbonate, and extracting and concentrating with isopropyl acetate, to obtain an oily matter;

mixing the oily matter with 16 g of ethyl bromobutyrate, 20 g of potassium carbonate and 300 ml of DMF, heating the resulting mixture to 70° C. for 48 hours, and cooling to ambient temperature;

adding 300 mL of NaOH at a concentration of 1N and stirring at ambient temperature for 3 hours, and extracting with isopropyl acetate to collect an aqueous phase; extracting the aqueous phase with methyl isobutyl ketone, to collect a methyl isobutyl ketone phase; and concentrating the methyl isobutyl ketone phase, to obtain the Elagolix sodium.

* * * * *